United States Patent
Meyer

(10) Patent No.: US 6,716,340 B2
(45) Date of Patent: Apr. 6, 2004

(54) WATER TREATMENT SYSTEM

(76) Inventor: Will Craig Meyer, 6435 Corbin Ave., Woodland Hills, CA (US) 91367

(*) Notice: Subject to any disclaimer, the term of this patent is extended or adjusted under 35 U.S.C. 154(b) by 0 days.

(21) Appl. No.: 09/782,270

(22) Filed: Feb. 12, 2001

(65) Prior Publication Data

US 2002/0153330 A1 Oct. 24, 2002

(51) Int. Cl.[7] .................................................. C02F 1/78
(52) U.S. Cl. ........................ 210/167; 210/188; 210/192; 210/194; 210/205; 261/75; 261/DIG. 11; 261/DIG. 42
(58) Field of Search ................................ 210/167, 188, 210/192, 194, 205; 261/75, DIG. 11, DIG. 42

(56) References Cited

U.S. PATENT DOCUMENTS

| | | |
|---|---|---|
| 3,610,417 A | 10/1971 | DeLoach |
| 4,172,786 A | 10/1979 | Frosch |
| 4,839,064 A | 6/1989 | McBurney |
| 4,981,594 A | 1/1991 | Jones |
| 5,106,497 A | 4/1992 | Finnegan |
| 5,174,901 A | 12/1992 | Smith |
| 5,186,841 A | 2/1993 | Schick |
| 5,494,589 A * | 2/1996 | Moorehead et al. |
| 5,879,565 A | 3/1999 | Kusmierz |
| 6,068,778 A * | 5/2000 | Steiner et al. |
| 6,086,772 A | 7/2000 | Tanimura |
| 6,342,154 B2 * | 1/2002 | Barnes |
| 6,372,148 B1 * | 4/2002 | Martin et al. |

FOREIGN PATENT DOCUMENTS

| | | |
|---|---|---|
| WO | WO 94/25150 | 11/1994 |
| WO | WO 98/31636 | 7/1998 |

* cited by examiner

Primary Examiner—Betsey Morrison Hoey
(74) Attorney, Agent, or Firm—Colin P. Abrahams

(57) ABSTRACT

A water treatment apparatus for treating water in a device using water as a circulating medium comprises an extractor line for removing water from the device and ozone generation means for producing and conveying a supply of ozone. A contactor/mixer member is provided and has an entry passage for receiving water from the extractor line and ozone from the ozone generation means. The contactor/mixer member has contacting passages for receiving a water and ozone mixture from the entry passage and is configured so as to create turbulence to intimately mix the water and ozone along at least a portion of its length. A return line is provided for receiving and transporting the water and ozone mixture from the contacting passages back to the device.

13 Claims, 2 Drawing Sheets

FIG. 3
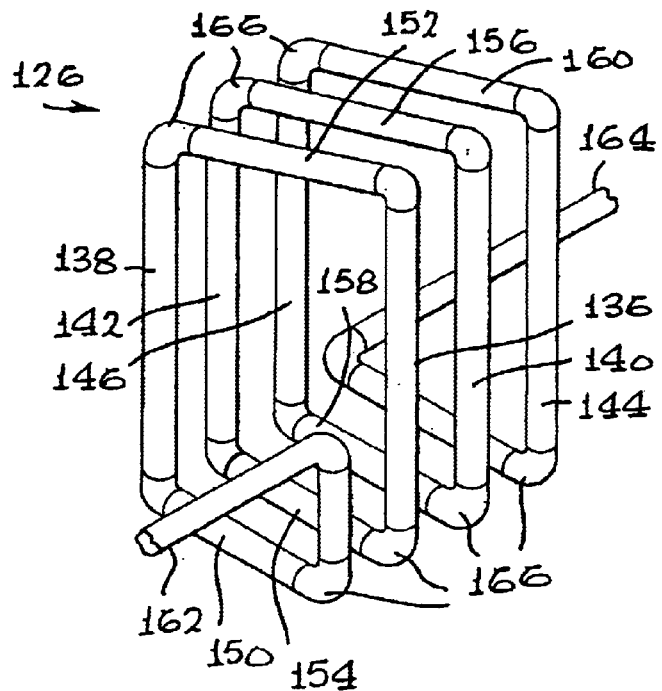
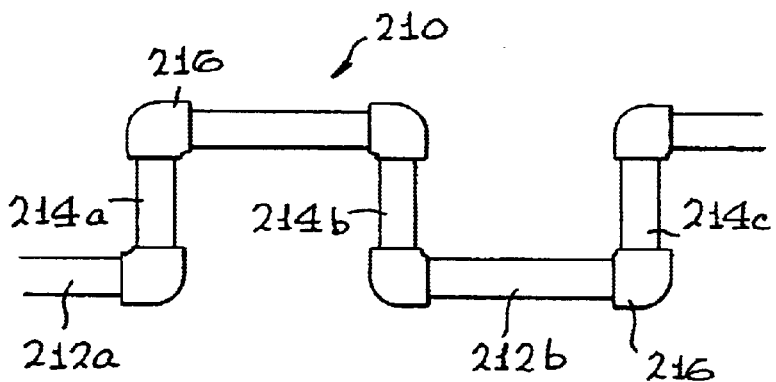
FIG. 4

WATER TREATMENT SYSTEM

FIELD AND BACKGROUND OF THE INVENTION

This invention relates to a water treatment system. More specifically, the invention is for treating water circulating in a device or machine, such as (but not limited to) a cooling tower using ozone, in order to remove from that water bacteria, viruses, yeast, mold, protozoa, algae and/or other biological or chemical components which not only affect the purity and effectiveness of the water in the device, but may also produce corrosion, scaling, oxidation and other effects which damage the hardware, including pipes and machinery containing the water. Removal of these components helps prevent disease, especially Legionella. The invention is also for a cooling tower or other water circulating machine including the water treatment system.

There are various patents in the literature which use cooling tower ozonation systems for inhibiting, reducing or otherwise eliminating biological and other components in aqueous solution systems. For example, U.S. Pat. No. 5,186,841 (Schick) describes a cooling water ozonation system for injecting ozone into a pressurized stream of aqueous solution, allowing the ozone injected stream to flow certain distances at certain velocities so that some of the ozone injected is dissolved. Schick has as an object of the invention the dissolution of increased amount of ozone in an effort to decrease the amount of ozone needed in the system.

U.S. Pat. No. 6,086,772 (Tanimura) describes a method and apparatus for preventing biofouling in cooling water systems by intermittently injecting concentrated ozone into a recirculating line of a cooling water system, in which cooling water is made to circulate in a closed system. U.S. Pat. No. 4,172,786 (Frosch) describes the ozonation of cooling tower water by continuously injecting ozone into water circulating between a cooling tower and heat exchanger so as to inhibit formation of further deposits, promote descaling of existing deposits, and inhibit chemical corrosion.

U.S. Pat. No. 5,106,497 (Finnegan) describes an ozone treatment system utilizing an airlift pump as a mixer and as a circulating means. This patent describes an invention for ozone treatment which eliminates the need for a circulating pump, making substantial energy savings.

Other patents related, but not pertinent, to the present invention of water treatment systems using ozone include: U.S. Pat. No. 4,981,594 (Jones); U.S. Pat. No. 5,879,565 (Kusmierz); U.S. Pat. No. 5,174,901 (Smith); U.S. Pat. No. 3,610,107 (DeLoach); U.S. Pat. No. 4,839,064 (McBurney), and International Applications WO 94/25150 (Rez-Tek) and WO 98/31636 (Enproamerica).

One of the reasons for treating the water in cooling towers (or any other machine circulating water as part of a cooling or purifying mechanism) is that such cooling towers have recently been recognized as a major source of Legionella infection. It is also recognized that ozone is a very effective biocide, small concentrations of which have been shown to have good performance in killing bacteria, yeasts and the like.

Appropriate dosing of ozone in water cooling systems is problematical with many formulae to calculate the amount of ozone needed to treat a given volume of water. Such formulae and calculations often do not take into account the fact that environmental conditions differ from one tower to another, as does the water, temperature and other parameters. Moreover, these parameters may change daily and seasonally at a particular cooling tower. The result has been a trend to use maximum ozone doses possible to ensure that enough ozone will be present to cover all extremes. However, ozone generators are expensive to install and maintain, and since ozone is only marginally soluble in water, excess production outgases into the atmosphere, often creating an offensive ozone smell.

Further, chillers and other hardware will react unfavorably when in contact with ozone. Corrosion is a significant result of high concentrations of ozone within a system. It should, however, also be recognized that while ozone itself may be corrosive, corrosion occurs from too much oxidant, rather than that of a specific type.

Ozone generators required to produce and regulate large amounts of ozone are often quite complex, expensive, require high voltage and current levels and a delicate balancing of power supplies. For these and other reasons, ozone generators are costly and have a poor reputation for dependability. Many existing ozone treatment systems for water simply dissolve as much ozone in the tower water as possible. Generators capable of producing large amounts of ozone are used to develop the maximum possible ozone residual in the tower basin water.

For any biocidal program to be effective, the water must be clean. Therefore, all cooling towers should have a filtration system of some kind, regardless of the biocidal technology used. The finest particles within the system have the greatest relative surface area, and produce the greatest chemical activity. They absorb chemicals used for disinfection or corrosion control, and also consume ozone. As such, and for maximum effectiveness of any water treatment program, particles in the 1–5 micron range, should preferably be removed. Various filter technologies are capable of doing this.

The ozone may be introduced by various methods, including sparging either in the sump itself or in a contacting tower. The contacting tower can also be fed by venturi injection. Another method of introducing ozone is by the aspiration thereof into flowing water with a venturi system. Although this can be effective, it requires a small diameter pipe with limited water volume and specific % pressure differential. When conditions are ideal, the gas and water will only remain mixed for a limited distance, and only then if the pipe is straight and of reasonably small diameter with no bends to increase back pressure.

SUMMARY OF THE INVENTION

According to one aspect of the invention, there is provided a water treatment apparatus for treating water in a device using water as a circulating medium, the apparatus comprising: (a) an extractor line for removing water from the device; (b) o z o n e generation means for producing and conveying a supply of ozone; (c) a contactor member having an entry passage for receiving water from the extractor line and ozone from the ozone generation means, and contacting passages for receiving a water and ozone mixture from the entry passage and configured so as to create turbulence to intimately mix the water and ozone along at least a portion of its length, and preferably its entire length; and (d) a return line for receiving and transporting the water and ozone mixture from the contacting passages back to the device.

According to another aspect of the invention, there is provided a water treatment apparatus for treating water in a cooling tower having a water basin, tower fill elements positioned over the water basin and through which water cascades downward for the purposes of cooling the water, the apparatus comprising: (a) a extractor line for removing water from the water basin for cleansing and purification treatment; (b) ozone generation means for producing and conveying a supply of ozone; (c) a contactor member having an entry passage for receiving water from the extractor line and ozone from the ozone generation means, contacting passages for receiving a water and ozone mixture from the entry passage and configured so as to create turbulence to intimately mix the water and ozone along at least a portion of its length, and an exit passage for the water and ozone mixture; and (d) a return line for receiving and transporting the water and ozone mixture from the exit passage, or multiple outlet passages, back to the top of the tower fill, the ozone being removed from the mixture by air stripping when the ozonated water cascades down the tower fill.

According to yet a further aspect of the invention, there is provided a method of treating water to remove bacterial and other impurities therefrom, the method comprising: (a) conveying a supply of water requiring removal of impurities to a receiving passage of a contactor member; (b) injecting a supply of ozone gas into the water in the receiving passage to form a water/ozone mixture; (c) passing the water/ozone mixture through a sealed non-linear passage having a plurality of bends therein to thereby create shear forces producing turbulence to maintain an intimate mixture of the water and ozone; (d) providing the non-linear passage with sufficient length so that the ozone in the water/ozone mixture has sufficient time to destroy at least a portion of the bacterial and other impurities in the water; (e) removing the ozone from the water/ozone mixture; and (f) conveying the purified or partially purified water to a predetermined location for further use.

In one aspect, therefore, the invention removes water to be treated from a sump or basin of a cooling tower system, pumps the water through a series of pipes and passages bent to create shear and turbulence, and introduces controlled amounts of ozone gas into the water as it passes through these passages. The turbulence resulting from the shearing of water flow around bends, preferably 90° bends, ensures proper mixing between the water and ozone gas, thus providing an extended opportunity for the ozone to carry out its biocidal activities on the water being so treated. Disinfection occurs in the pipes where the ozone and water are mixed, and the ozone and water are thereafter conveyed in appropriate passages to the top of the cooling tower.

In one aspect, the ozone contacting and mixing with water is accomplished in a contactor device comprised of pipe lengths of predetermined length, preferably about 3 feet long, each of which is connected to horizontal sections, also of predetermined length and preferably approximately 6 inches long. The connection between the vertical pipes and horizontal sections is through an approximately 90° elbow. This construction results in a somewhat helical configuration, and facilitates the use of considerable lengths of pipe in a substantially small volume of space.

The vertical and horizontal sections together form a continuous passage through which water is forced, and when the water passes through a 90° elbow or bend, the flow of the water is sheared, producing turbulence. This happens at every elbow turn, and at every 90° bend. In normal circumstances, the tendency for the water and the ozone gas is to separate, but this is countered at every turn along the length of the passage.

Depending upon the flow rate and the pressure produced by the pump driving the water through the passage, pipes of any suitable diameter and length can be used. A prototype system used approximately 30 feet of 2.5 inch diameter piping, consisting of 5 pipe loops, but systems can be scaled up or tailored so as to be of appropriate size and length for any particular system.

This ozone contacting mechanism for contacting and mixing the ozone gas with the water has benefits not displayed by conventional venturi feeds, inline helical mixers, mixing towers or direct sparging. The contactor described herein causes and maintains intimate contact between the gas and water for an extended mixing length, and sustains this intimate contact more than any other system. It is also fairly inexpensive to build. Importantly, the contactor treats the water in the confined spaces of the piping where bacteria, particles and dissolved chemicals are in contact with the ozone gas phase as well as the dissolved phase. Since ozone is much more concentrated and active in the gaseous phase, the effectiveness of the ozone gas action on the bacteria etc. is increased, thereby allowing relatively low ozone levels to have considerably more effect than much higher concentrations of ozone would have in standard systems that use only the dissolved residual. Therefore, a significant aspect of the present invention is the use of ozone in its active gaseous phase, as opposed to its dissolved phase, for enhanced action against bacteria, other microbiota and dissolved components.

The dissolved and/or gaseous mixture is confined in the pipes comprising the contactor device where the actual disinfection of bacteria, yeasts and other impurities in the water occurs. In contrast to other systems which endeavor to develop high dissolved residuals of ozone in the water, and thereafter convey the ozonated water to the tower to treat the sump, the present system treats the water in the contactor/mixer device, and then returns the water to the sump, already treated and stripped of ozone. Since the water is already disinfected in the contactor device, there is, of course, no need to develop an ozone residual in the sump itself. In fact, the ozone, both residual and gaseous, is removed from the water (as will be described below) before the water reaches the sump, and this ensures that almost any possible corrosion which may be caused when ozonated water passes from the sump to the chiller is prevented. This is accomplished by using the natural tendency of a cooling tower to airstrip water as it passes over the fill elements. Ozonated water from the contactor device is piped into the top of the fill elements, where it is allowed to cascade over the fill from the top of the tower. As it cascades, residual gases, which include ozone, are stripped from the water by the time it reaches the sump. In this way, the benefit of treating the fill elements with ozonated water, and thereby disinfecting them, is achieved. This is in contrast to many other, if not all, existing systems which do not disinfect the fill elements.

Additionally, when the fan of the cooling tower is on, the ozone is outgassed with the aerosol plume, disinfecting it to some degree. Since it is the aerosol plume that spreads Legionella, an important aspect of the invention is therefore the effect of the ozone on the plume itself, causing this disinfection.

Another important aspect of the present invention relates to the treatment of so-called "protected areas or surfaces" within the cooling tower sump. Such protected surfaces and areas may comprise surfaces, corners, recesses, and other nooks and crannies which are by-passed by the water circulating through the sump and cooling tower. The surfaces and recesses generally do not contact water containing disinfectants of any type. These protected areas are more readily able to harbor microbial populations which are therefore not exposed to the biocide, either a chemical biocide or ozonated water, being used to treat the water in the cooling tower, and will therefore form "hot spots" of biological activity. In many instances, these protected areas are visible to the naked eye, since they harbor algae or diatoms, forming green or brown coatings on the hardware. Previous systems have attempted to prevent the formation of such biological activity in the protected areas, often unsuccessfully, by developing high residual concentrations of biocide in the sump water in the hopes that sufficient biocide will be present to penetrate to these protected areas, and therefore kill the microbes which are located therein.

In the present invention, the ozone is substantially stripped from the water before it enters the sump once more, and these protected surfaces and recess can be a source of reinfestation of the water. Therefore, in an aspect of the invention, the water treatment system of this invention taps or diverts a flow of ozonated water from the contactor device, before the ozone has been stripped from the water. This tapped flow is diverted through appropriate tubing and passages to outlets, such as nozzles, which can be specifically positioned in the sump, exactly where needed, to direct a small flow of ozonated water to one of these protected areas for spot treatment. In this way, the invention allows for such trouble areas to be treated effectively, but without introducing enough ozone into the sump water to cause corrosion in the sump or chiller loop.

An advantage of the system of the present invention is that it may be less costly to construct and maintain than comparable systems on the market. This is due to the simplicity of its design, and, notably, the fact that there is no need to produce huge quantities of ozone. Since small amounts of ozone are produced, and can be used effectively in the confined space of the contacting device, comparatively little ozone is needed compared to those systems where water in the sump itself is treated with the biocide. As a result, the system may require little in the way of controls, and a single ozone generator would be adequate for most towers. Of course, an appropriate generator can be used, which can be scaled up or down, as the situation requires, for the economical treatment of any size system, as well as the fluctuations in environmental conditions which may require more or less ozone at any particular point in time.

BRIEF DESCRIPTION OF THE DRAWINGS

FIG. 3 is a more detailed perspective view of the contactor device in one embodiment of the water cooling system of the invention; and FIG. 4 is a more detailed perspective view of the contactor device in another embodiment of the water cooling system of the invention.

DETAILED DESCRIPTION OF THE INVENTION

The invention relates to a method and apparatus for cleansing, disinfecting and purifying water circulated in a cooling tower having a sump, reservoir or water basin and fill elements thereabove. In accordance with this invention, water is removed, preferably from the sump, of the cooling tower and treated with ozone which acts as a biocide while cleansing the water of dissolved organisms or other components. The treated water is thereafter returned to the water cooling tower, preferably to the top of the fill elements. The invention seeks to purify the water by injecting ozone gas into water side lines or passages, keeping the water turbulent by agitating shearing actions where the ozone remains as a gas, at least partially, and is most active.

Figure 1:
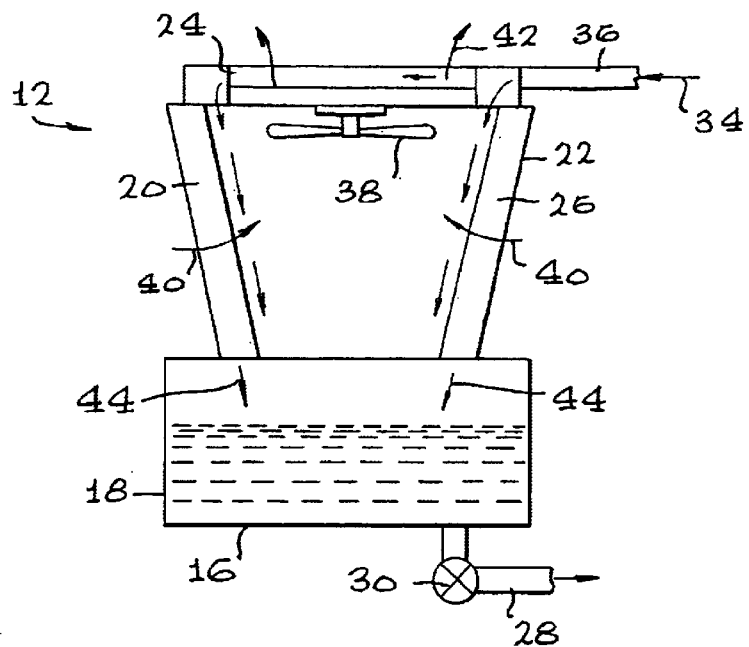
FIG. 1 is a diagrammatic representation of a cooling tower system typical of the prior art.

Reference is now made to FIG. 1 of the drawings, which shows a prior art cooling tower. In FIG. 1, a cooling tower 12 basically comprises a water basin or sump 14, having a base 16 and side walls 18. The tower 12 comprises almost vertical but somewhat inclined fill elements 20 and 22, and a top deck tanks 24 to receive water from the chiller (not shown). Holes in the tank bottom allow the water to drain through the fill for cooling. Attached to the base 16 of the sump 14 is a pipe 28, and a pump 30 located along the pipe. Cooled water, identified by reference numeral 32, is removed from the sump 14 and, by the action of the pump 30, flows through the pipe 28 to a chiller or other machine requiring cool water for use in the cooling process. During the course thereof, the water is heated, and eventually this warm water, identified by reference numeral 34, is returned through pipe 36 to the top deck tanks 24 of the cooling tower. Using appropriate passages, the warm water runs downward through the fills 20 and 22, where it is cooled.

A fan 38 is located on the top deck 26, and is designed such that, when rotating, causes air flow from outside of the fills 20 and 22, through the fills as indicated by arrows 40. The air passes through the top deck 26, as indicated by arrows 42 and is expelled into the atmosphere. As the warm water passes through the fills 20 and 22, it is cooled, facilitated by the flow of air through the fills as indicated by arrows 40 and 42. The water cascading down the fills 20 and 22 at the lower ends thereof is therefore significantly cooled, and flows or falls back into the sump 14, as indicated by arrows 44, to become part of the cool water 32. The cycle is repeated with the water acting as a cooling medium for the chiller or other apparatus.

As has been described above, the water used in the cooling tower, and circulated to the chiller, becomes infected with algae, bacteria, as well as other microbial and dissolved minerals, and it is necessary to cleanse and purify this water in order to ensure the proper functioning of the system.

Figure 2:
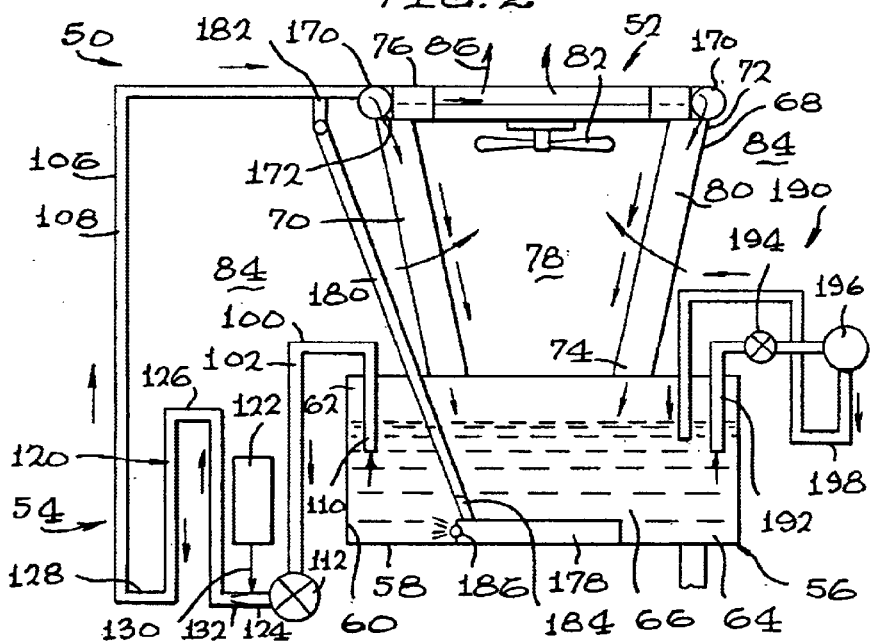
FIG. 2 is a diagrammatic representation of the water treatment system of the invention.

Reference is now made to FIG. 2 of the drawings which shows a diagrammatic representation of one embodiment of the water treatment apparatus of the invention. In FIG. 2, there is shown a cooling tower and water treatment system 50 comprising a water tower 52 and water treatment device 54 in association therewith. The water tower 52 is of generally conventional construction, and comprises a water basin or sump 56 having a base 58 and side walls 60. The top 62 of the sump is generally open, and the base 58 and side walls define a water basin 64 which, in use, contains cooled water 66. Above the sump 56 are cooling tower fill elements 68 and 70, which may be made up in a number of ways, and may consist of a singular circular configuration, four side panels, or some other configuration, whether open or closed. The fill elements 68 and 70 are of generally frusto-conical shape, tapering from the top end 72, down to the lower end 74, with the lower end 74 being positioned above or below the water level in the sump 56 so that water flowing or cascading down the fill elements 68 and 70, described below, falls into the water basin 64. The water tower 52 further comprises a top deck tank 76 over the fill elements 68 and 70, creating a partially enclosed space 78. The top deck tank 76 includes piping and passages as will be described below for conveying the circulating water to the fill elements 68 and 70 en route to the water basin 64.

Suspended from a top deck 75 is a fan 82, which, when activated, is configured so that upon rotation air is drawn into the space 78 from the outside, indicated by reference numeral 84, the air passing through fill elements 68 and 70 into the space 78 and out through openings in the top deck 75 for discharge into the atmosphere as a plume 86.

The water treatment device 54 associated with the water tower 52 comprises a pipe 100 defining an exit passage 102, ozone treatment apparatus 104, and a pipe 106 defining a return passage 108. The pipe 100 has an open end 110 which is in the water 66 of the water basin 64 so as to extract water therefrom, while the pipe 106 defines the return passage for conveying water from the ozone treatment apparatus to the top deck tanks 76 of the water tower 52. The direction of water flow is from the water basin 64, to the ozone treatment apparatus 104, and through the return passage 108 to the top deck tanks 76, where the water cascades down the fill elements 68 and 70, back into the water basin 64. This flow is facilitated by a pump 112, located in pipe 100 in the embodiment shown, although a pump may be situated in any position which is suitable in the circumstances.

The ozone treatment apparatus 104, located between pipe 100 and pipe 106, comprises a contactor device 120, and an ozone generator 122. The contactor/mixer device comprises an entry pipe 124, a series of flow deflector pipes 126, and an exit pipe 128. The entry pipe 124 is connected with pipe 100, and receives water therefrom, while the exit pipe 128 discharges water from the contactor device 120 into the pipe 106.

The ozone generator 122 is of a conventional type, the size, output and other characteristics and properties of which can be varied or adjusted either manually or in response to preset criteria. The ozone generated by the ozone generator 122 is conveyed through ozone passage 130 to a venturi injector 132, so that ozone gas enters the water stream flowing through the entry pipe 124. The ozone gas and water are therefore mixed, and the mixture is conveyed to the flow deflector pipes 126 of the contactor/mixer device 120.

Reference is now made to FIG. 3 of the drawings which shows one embodiment of the flow deflector pipes 126 in accordance with the invention. It is to be understood that the flow deflector pipe configuration 126 shown in FIG. 3 is merely one example of the type of configuration which may be used, and variations in the length, number of pipes and vertical/horizontal distances between the pipes can be varied to best suit the circumstances, and to optimize the effect of the ozone gas within the water, as considered necessary.

The flow deflector pipes 126 comprises six vertical pipes 136, 138, 140, 142, 144, and 146, connected, as will be described below, with six horizontal pipes 150, 152, 154, 156, 158 and 160. Further, the flow deflector pipes 126 include a water entry pipe 162 and a water exit pipe 164 by means of which water is respectively introduced into and exhausted from the flow deflector pipes 126. The vertical and horizontal pipes are connected to each other by a series of substantially right-angled elbow connectors 166 so as to provide a continuous, helical, flow passage extending from the water entry pipe 162 to the water exit pipe 164. It should be noted, of course, that the contactor/mixer can be stretched out and not helical, and be of any suitable shape such as zig-zag, squared and the like.

A water and ozone gas mixture enters the water entry pipe 162, flows through a first elbow joint 166 and into the horizontal pipe 150. The horizontal pipe 150 is connected to vertical pipe 138 by an elbow joint 166. By means of a series of elbow joints 166, vertical pipe 138 connects to horizontal pipe 152, which connects to vertical pipe 136, connecting to horizontal pipe 154, connecting to vertical pipe 142, connecting to horizontal pipe 156, connecting to vertical pipe 140, connecting to horizontal pipe 158, connecting to vertical pipe 146, connecting to horizontal pipe 160 and finally to vertical pipe 144. From the vertical pipe 144, the water is conveyed to the water exit pipe 164, which is connected to the exit pipe 128 of the contactor 104.

As has been described elsewhere in this specification, the ozone is most active and effective when in a gaseous state, and the flow deflector pipes 126 help to contain undissolved ozone gas in the ozone/water mixture. As the water with ozone passes through the various vertical and horizontal pipes, considerable turbulence is created by shear forces as the water passes through each of the elbow joints 166, causing a change in flow direction. Therefore, the system is designed so as to keep the ozone gas entrained within the water over the length of the flow deflector pipes, and thereby achieve considerable biocidal effects with only a minimal amount of ozone. Since the system is a closed one, confined and under the effects of considerable turbulence, the water and its impurities are subjected to an intense level of ozone activity to thereby purify it.

As shown in FIG. 2, the exit pipe 128 receives a mixture of water and gaseous and dissolved ozone, which is conveyed through the pipe 106 to a distribution pipe 170 in or adjacent the top deck 75. The distribution pipe 170 generally is located above the fill elements 68 and 70, and conveys water from the pipe 106 through apertures or ports 172 as required, so that the water flows down through the fill elements 68 and 70.

It will be noted that most of the disinfection of the water occurs in the contactor device 120 so that water entering the pipe 106 and distribution pipe 170 has to a large extent, or completely, been disinfected. However, ozone still remains in the water as it passes through the pipe 106, and enter the distribution pipe 170.

As the water runs down through the fill elements 68 and 70, the fill elements surfaces are exposed to ozonated water, continuing the biocidal activity of the ozone. The fan 82 draws in air from the outside 84 into the space 78 and out into the atmosphere in a plume 86 containing air water vapor, water droplets and entrained microbiota and dissolved contaminants. The movement of air in this manner both cools the water as it passes through the fill elements 68 and 70, and further subjects the ozonated water to air stripping to remove the remaining ozone. Generally, an increase in air flow enhances the efficiency of the air stripping of ozone from the water cascading down in the fill elements 68 and 70.

The flow deflector pipes 126 in the present embodiment comprise vertical pipes of approximately 3 feet in length, with horizontal connecting sections of about 6 inches in length. Each are connected by 90° elbows to produce a helical configuration, and thus able to pack considerable lengths of pipe into a small volume of space. The diameter of the pipes are approximately 2.5 inches. It will, of course, be appreciated that the number of vertical and horizontal pipes can be varied depending upon the system, and their relative length and number can be adjusted, as well as the diameter of the tube.

While the system described above removes water from the sump 56, treats it with ozone and then returns it to the water tower 52, it should be appreciated that, while this method of purification is highly effective and substantially removes impurities from most of the water, there will be recesses or protected surfaces and areas in the sump where circulation is minimal and/or non-existent. In these areas, the effects of the purification process by circulating the water to the water treatment device 54 will therefore not be felt. Therefore, and in accordance with another aspect of this invention, a mechanism for "spot treating" areas within the sump 56, where bacterial and other impurity levels are likely to rise due to a lack of circulation, is provided. The spot treatment mechanism is a flexible one, with adjustments possible to direct its effect to the area(s) needed.

The spot treatment mechanism comprises a support 178 or other movable mechanism which rests on the base 58 of the sump 56. A flexible hose 180 extends from the pipe 106, to which it is connected by an adjustable valve 182 located at a point along the pipe 106 near the distribution pipe 170. The hose 180 extends from the valve 182 to a connector 184 by means of which it is secured to the support 178. The support 178 has a jet nozzle or outlet 186. On an as-needed basis, the ozone plus water mixture can be drawn off from pipe 106 through the valve 182, flowing through the hose 180 and into the support 178. The position of the sweeper can be varied, by moving it across the base 58, or otherwise within the sump 56, so that the jet nozzle 186 is located directly adjacent an area requiring spot treatment. By an appropriate pump mechanism within the support 178, or simply by the force of the ozone and water moving through the hose 180 when the valve 182 is opened, ozonated water is discharged from the jet nozzle 186 directly onto an area where biocidal action is required.

In one embodiment of the invention, the support 178 has a magnetic base, by means of which it remains in position on the base 58, but can nevertheless be moved on an as-needed basis, depending upon the area which will require spot treatment.

With reference to FIG. 2, there is also shown a filtering device 190 (such as a sand filter, bag, cartridge etc.), comprising a filter or centrifugal separation system which is separate from the ozone treatment system. While the filtering system 190 is shown as a separate component in the embodiment of FIG. 2 of the drawings, the ozone treatment system and the filtering device can, however, be combined into a single mechanism so as to use one pump. The filter device 190 extracts water from the sump 56 through pipe 192 by action of pump 194. The water then passes to a filter 196 and, duly filtered, is returned to the sump 56 through return pipe 198.

FIG. 4 shows an alternative embodiment of a contactor/mixer 210 having horizontal sections 212a, 212b etc. connected by elbow joints 216 to vertical sections 214a, 214b, 214c etc. Water/ozone turbulence is created in the non-linear passages defined by the sections 212 and 214.

Representative examples of the application of the water treatment device of the invention will now be provided.

EXAMPLE 1

A prototype or test water treatment system of the invention was installed on a 100 ton BAC (Baltimore Air Coil) cooling tower serving the theater at a performing arts building at a college in Los Angeles, Calif. The water treatment system was installed in July 2000, and has been running continuously since then. Bacterial levels were monitored by heterotrophic plate counts using standard methods. Since it is well documented that ozone is effective at killing the spectrum of microbes, including Legionella and the protozoa that harbor this bacterium, it is considered that a simple heterotrophic plate count is a good indicator of overall bactericidal effect of the ozone when this disinfectant is used.

Prior to the installation of the system of the invention, the cooling tower had been treated using pool chlorine tablets as a disinfectant, with the tablets being contained in a perforated one gallon plastic jug located in the sump. At the commencement of the installation of the water treatment system of the invention, this chlorine and other chemical treatment methods were discontinued, the water drained, and thereafter replaced before ozonation in accordance with the invention began. Samples for plate counts were collected in the approximate middle of the sump in order to detect the presence of planktonic bacteria which may be included in the aerosol plume produced by the tower. In addition, "wipe down" samples can be taken from surfaces of the sump in corners and circulation nodes, as determined by, for example, dye tracer techniques, to test the effectiveness at disinfecting the water and surface bound populations.

Measurements near the beginning of the operation resulted in planktonic plate counts "too few to count" as would be expected, since the sump had been filled with water of regulated drinking purity. Thereafter, plate counts were made at regular intervals. All measurements resulted in "too few to count" results, most being actually zero or close to zero. Generally, the standards methods require, to be statistically valid, a plate count should have at least 30 cfu (colony forming units). Anything lower than this level is reported as "too few to count" or TFTC.

The following results were obtained:

TABLE 1

Plate Counts

| Date | Plate Count (cfu) |
| --- | --- |
| 08/15/00 | TFTC |
| 09/12/00 | TFTC |
| 10/09/00 | TFTC |
| 10/19/00 | TFTC |
| 11/13/00 | TFTC |
| 11/27/00 | TFTC |

As a basis for comparison, regulated drinking water allows for 500 cfu as acceptable. In the present application of the invention, where measurements were taken, plate counts did not ever exceed 12 cfu, except during one portion of the experiment when the ozonator was turned off for four days. In this regard, it should be noted that towers with chemical treatment often reach plate counts nearing one million (1,000,000) cfu, and these are considered acceptable by the chemical water treatment companies.

In conjunction with the plate counts, the ozone levels in the system were monitored on a regular basis. These measurements were made with a Hach Indigo Ozone Kit. The ozone levels were measured after the water samples were allowed to sit for long enough time for the entrained gas bubbles of ozone to clear, ensuring the measurement of dissolved ozone was not confounded with measurements of ozone in the gaseous phase. The ozone levels in the water exiting the contactor device averaged 0.28 mg/L, well into the concentration range for effective disinfection. At the same time, water in the sump which had passed through the fill elements and had been subject to the air stripping treatment over the fill elements showed no detectable ozone in all cases. This is consistent with expectations of ozone removal for prevention of corrosion in the heat exchange elements. Copper, and soft iron corrosion coupons, exposed to the sump water for 5 months showed no visible evidence of corrosion. The results therefore confirm that excellent levels of disinfection were being provided, with minimal amounts of ozone entering the cooling tower and hardware which could result in corrosion and damage.

Bacterial colonization of surfaces was monitored by wiping a suspect surface with sterile gauze and agitating the gauze in 100 ml of water collected from the center of the sump. When this suspect surface was subjected to spot treatment in accordance with the invention as described above, the results were TFTC. Therefore, the spot treatment was shown in this example to be effective at eliminating "hot spots" missed by the treatment of the water by the circulation methods and ozone generator of the invention, as described above.

EXAMPLE 2

Dosing experiments were also conducted, since finding the optimal or appropriate dosage of ozone injection into a system is a problem for all ozone systems. In order to address and resolve this problem, an experiment was conducted whereby the ozonator was turned off for four days, and the plate counts measured daily until an unacceptable level of bacteria had developed in the sump water. At the beginning of the study, the plate counts were 700 cfu/ml. The experiment was, at least to some extent, influenced by the surroundings and use of the cooling tower and, since it was carried out at a college, the dosing experiments were conducted at times when classes were not in session, limiting the amount of time the tower could go untreated. Further, the counts were not allowed to go too high, and about 700 cfu/ml was considered adequate for the test. The average water temperature during the study was 68° F.

The ozonator was turned on in the morning at approximately 8:00 am, and plate count samples were collected at 2 hour intervals throughout the day for the first 8 hours, and at 24 hours. It was expected that the ozone would reduce the bacteria levels in a progressive manner, allowing development of a decay-curve from the data. This decay-curve would then be used to determine dosing in terms of how much time the ozonator should be operational each day in order to obtain acceptable disinfection. Somewhat unexpectedly, the bacteria count was zero (TFTC) in the first 2-hour count, and stayed TFTC from that point onward. Since the system water volume in the example under discussion is 500 gallons, it was concluded that 2 hours operation per day was adequate dosing for 500 gallons of water. The ozone output during the study was 10 gms/hour, as measured by a spectrometric ozone analyzer, and confirmed by on site measurements, using "precision gas defector tubes" supplied by Matheson Safety Products.

The dosing experiments further consisted of the installation of a timer that limited ozone production to 2 hours per day from this point in the study. Plate counts remained zero, or TFTC, throughout the study. For the system tested, the dosing formula was therefore a simple 2 hours per day, per 500 gallons of water. This dosing can, however, be monitored and changed according to the seasons and the conditions. For example, in the warmer months, the dosage may be increased to 3 hours per day to provide a comfortable margin of error, considering the higher bacterial activity at warmer temperatures. This change can be easily achieved for larger systems by increasing the hours of operation, and/or using additional generators in parallel, if required, for really large systems. Further effectiveness would be expected from lengthening the contactor device so that the tube length would be increased, which of course would allow the water to reside in contact with the ozone for longer periods of time before being air stripped.

The following results were obtained.

TABLE 2

Dosing Experiment

| Time (hour) | Plate Count (cfu) |
| --- | --- |
| 0 | 730 |
| 2 | TFTC |
| 4 | TFTC |
| 6 | TFTC |
| 8 | TFTC |
| 24 | TFTC |

The results of the water treatment system of the invention indicate a high level of disinfection of both the water, sump, fill surfaces, and some disinfection of the aerial plume is an expected additional benefit. Dosing is tailored by reducing ozone introduction to the water to a time of operation that can be fine-tuned at the particular site to obtain the desired level of microbial control. The corrosion problem is significantly reduced or even eliminated by sending only de-ozonated water to the corrodible components. The system is simple to manufacture, inexpensive and dependable.

While invention has been described above mainly with reference to use on or with cooling towers, it has many other applications and these specifically form part of the invention. For example, water treatment system and device may be used in: aqua culture (fish farms); agriculture, to increase shelf life for example; waste water treatment systems; color removal; toxin removal applications; heavy metal removal; hospital water treatment systems; and hotel and big building water systems. In short, the water treatment system of the invention can be used to treat water in any system or device which generally requires or uses circulating water which must be maintained in a clean and disinfected condition.

Since the ozone does not enter the water in the sump (or other part of any device to which it may be attached), the sump can contain or be made of a material which may otherwise be damaged or rendered ineffective by ozone. Examples of such materials are copper and silver.

The invention is not limited to the precise details which are described herein.

What is claimed is:

1. A water treatment apparatus for treating water in a device using water as a circulating medium, the apparatus comprising:

(a) an extractor line for removing water from the device;

(b) ozone generation means for producing and conveying a supply of ozone, (c) a contactor/mixer member having an entry passage for receiving water from the extractor line and ozone from the ozone generation means, and a contacting passage for receiving a water and ozone mixture from the entry passage and configured so as to create turbulence to intimately mix the water and ozone along at least a portion of its length wherein the contacting passage has a plurality of deflecting baffles therein wherein water and ozone gas flowing in the water/ozone mixture passage is subjected to shear at the deflecting baffles; and (d) a return line for receiving and transporting the water and ozone mixture from the contacting passages back to the device.

2. A water treatment apparatus as claimed in claim 1 wherein the extractor line includes a pump for conveying water through the extractor line and contactor/mixer member.

3. A water treatment apparatus as claimed in claim 1 wherein ozone generation means comprises an ozone generator, an ozone passage and a venturi injector through which generated ozone is introduced to the entry passage of the contactor/mixer member.

4. A water treatment apparatus as claimed in claim 1 wherein the contacting passage comprises a series of pipes connected to each other in a non-linear arrangement to provide a water/ozone mixture passage having bends therein, wherein water and ozone gas flowing in the water/ozone mixture passage are subjected to shear at the bends to produce turbulent mixing in the pipes.

5. A water treatment apparatus as claimed in claim 1 further comprising a spot treatment device for treating selected areas in the device with doses of a water and ozone mixture.

6. A water treatment apparatus as claimed in claim 5 wherein the spot treatment device comprises a support, a flexible hose through which is diverted a portion of water and ozone mixture downstream of the contactor member, and jet nozzles for ejecting the water and ozone mixture to a preselected location.

7. A water treatment apparatus as claimed in claim 6 further comprising magnetic means for anchoring the support at the preselected location.

8. A water treatment apparatus as claimed in claim 1 wherein the device using water as a circulating medium is a cooling tower having a water basin and tower fill elements above the water basin, and the return line transports the ozone and water mixture to a position at or near a top end of the fill elements of the device.

9. A water treatment apparatus as claimed in claim 1 further comprising a filter for removing particulate matter from water in the device.

10. A water treatment apparatus for treating water in a cooling tower having a water basin, tower fill elements positioned over the water basin and down which fill elements water cascades for the purposes of cooling the water, the apparatus comprising:
(a) a extractor line for removing water from the water basin for cleansing and purification treatment;
(b) ozone generation means for producing and conveying a supply of ozone;
(c) a contactor/mixer member having an entry passage for receiving water from the extractor line and ozone from the ozone generation means, a contacting passage for receiving a water and ozone mixture from the entry passage and configured so as to create turbulent mixing of water and ozone along at least a portion of its length, and an exit passage for the water and ozone mixture; and
(d) a return line for receiving and transporting the water and ozone mixture from the exit passage back to the tower fill elements of the device, ozone being removed from the mixture by air stripping when cascading down the fill elements.

11. A water treatment apparatus as claimed in claim 10 wherein the contacting passage comprises a series of pipes connected to each other in a non-linear arrangement and comprised of a plurality of substantially vertical pipes connected at right angles to a series of substantially horizontal pipes to form a helix-like configuration, thereby providing a water/ozone mixture passage having bends therein, wherein water and ozone gas flowing in the water/ozone mixture passage is subjected to turbulence at the bends.

12. A water treatment apparatus for treating water in a device using water as a circulating medium, the apparatus comprising:
(a) an extractor line for removing water from the device;
(b) ozone generation means for producing and conveying a supply of ozone,
(c) contractor/mixer member having an entry passage for receiving water from the extractor line and ozone from the ozone generation means, and a contacting passage for receiving a water and ozone mixture from the entry passage and configured so as to create turbulence to intimately mix the water and ozone along at least a portion of its length, wherein the contacting passage comprises a series of pipes connected to each other in a non-linear arrangement to provide a water/ozone mixture passage having bends therein, wherein the series of pipes comprises a plurality of substantially vertical pipes connected at right angles to a series of substantially horizontal pipes to form a helix-like configuration; and
(d) a return line for receiving and transporting the water and ozone mixture from the contacting passage back to the device.

13. A water treatment apparatus as claimed in claim 12 wherein the vertical pipes are each approximately three feet in length, the horizontal pipes are each approximately six inches in length, the diameter of the vertical and horizontal pipes are approximately 2.5 inches, and ends of each vertical and horizontal pipe are connected to ends of its adjacent horizontal and vertical pipes respectively by a substantially right angled elbow joint.

* * * * *